United States Patent
Lockwood et al.

(10) Patent No.: US 10,016,599 B2
(45) Date of Patent: *Jul. 10, 2018

(54) DEVICES, SYSTEMS, AND METHODS FOR TREATING OBSTETRIC AND GYNECOLOGICAL DISORDERS

(71) Applicant: Ohio State Innovation Foundation, Columbus, OH (US)

(72) Inventors: Charles Lockwood, Bexley, OH (US); Edmund Funai, New Albany, OH (US); Ali R. Rezai, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/440,705

(22) Filed: Feb. 23, 2017

(65) Prior Publication Data
US 2017/0157397 A1    Jun. 8, 2017

Related U.S. Application Data

(63) Continuation of application No. 14/850,089, filed on Sep. 10, 2015, now Pat. No. 9,616,226, which is a continuation-in-part of application No. PCT/US2014/022423, filed on Mar. 10, 2014.

(60) Provisional application No. 61/776,046, filed on Mar. 11, 2013.

(51) Int. Cl.
*A61N 1/00* (2006.01)
*A61N 1/36* (2006.01)
*A61N 1/05* (2006.01)

(52) U.S. Cl.
CPC ....... *A61N 1/36007* (2013.01); *A61N 1/0521* (2013.01); *A61N 1/0551* (2013.01); *A61N 1/36071* (2013.01); *A61N 1/36107* (2013.01); *A61N 1/36139* (2013.01); *A61N 1/36171* (2013.01)

(58) Field of Classification Search
CPC .............. A61N 1/36007; A61N 1/0521; A61N 1/36107; A61N 1/36139; A61N 1/36071
See application file for complete search history.

(56) References Cited

U.S. PATENT DOCUMENTS

| | | |
|---|---|---|
| 3,866,613 A | 2/1975 | Kenny |
| 4,827,946 A | 5/1989 | Kaali et al. |
| 5,716,377 A | 2/1998 | Rise et al. |
| 6,402,683 B1 | 6/2002 | Marty et al. |

(Continued)

OTHER PUBLICATIONS

International Search Report dated May 13, 2014 for corresponding Patent Application No. PCT/US2014/022423.

(Continued)

*Primary Examiner* — Rex R Holmes
(74) *Attorney, Agent, or Firm* — FisherBroyles, LLP; James W. Hill

(57) ABSTRACT

One aspect of the present disclosure relates to a therapy delivery device for treating an obstetric or gynecological disorder other than urinary incontinence in a subject. The therapy delivery device can include a housing, at least one electrode, and a power source. The housing can be configured for implantation in a reproductive system of the subject. The at least one electrode can be connected to the housing and be configured to deliver an electrical signal to an autonomic nervous system nerve target. The power source can be in electrical communication with the at least one electrode.

19 Claims, 8 Drawing Sheets

(56) References Cited

U.S. PATENT DOCUMENTS

| 6,432,037 B1 | 8/2002 | Eini et al. |
|---|---|---|
| 2005/0143788 A1 | 6/2005 | Yun et al. |
| 2005/0153885 A1 | 7/2005 | Yun et al. |
| 2005/0277998 A1 | 12/2005 | Tracey et al. |
| 2006/0079943 A1 | 4/2006 | Narciso, Jr. |
| 2007/0142879 A1 | 6/2007 | Greenberg et al. |
| 2007/0167992 A1 | 7/2007 | Carley |
| 2010/0004707 A1 | 1/2010 | Hochman et al. |
| 2010/0144691 A1 | 6/2010 | Yun et al. |
| 2011/0224749 A1 | 9/2011 | Ben-David et al. |
| 2012/0109233 A1* | 5/2012 | Lee .................. A61F 7/007 607/3 |
| 2014/0067021 A1 | 3/2014 | Rezai et al. |
| 2014/0081355 A1 | 3/2014 | Marsh et al. |

OTHER PUBLICATIONS

European Examination Report dated Jul. 11, 2017 for corresponding European Application No. 14717905.5.
EPO, Examination Report for European Patent Application No. 14717905.5 of Ohio State Innovation Foundation, dated Nov. 11, 2016, 5 pgs.
Karsdon, Jeffrey et al., "Electrical inhibition of preterm birth: Inhibition of uterine contractility in the rabbit and pup births in the rat", Am J Obstetrics Gyn 193, 1986-93 (2005).
Kothari, Truptesh H. et al., "Inhibitory effects of electrical stimulation on delivery in pregnant rats", Europ J Obstetrics Gyn Reproduct Biol 141 18-22 (2008).

* cited by examiner

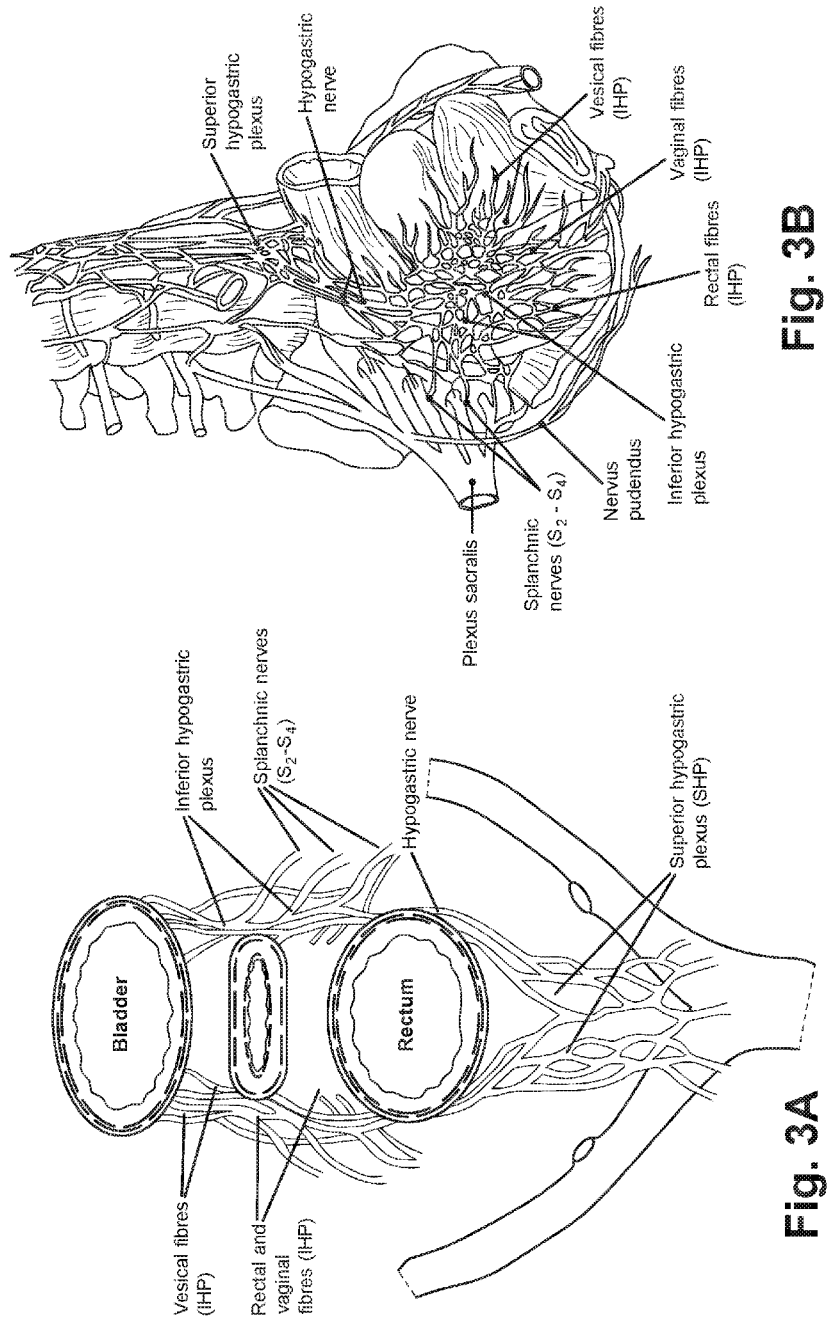

DEVICES, SYSTEMS, AND METHODS FOR TREATING OBSTETRIC AND GYNECOLOGICAL DISORDERS

RELATED APPLICATION

This application is a continuation of U.S. patent application Ser. No. 14/850,089, filed Sep. 10, 2015 and now U.S. Pat. No. 9,616,226, which is a continuation-in-part application of PCT Application Serial No. PCT/US2014/022423, filed on Mar. 10, 2014 and now expired, which claims priority to U.S. Provisional Patent Application Ser. No. 61/776,046, filed Mar. 11, 2013, the entirety of all applications is hereby incorporated by reference for all purposes.

TECHNICAL FIELD

The present disclosure relates generally to neuromodulatory devices, systems and methods, and more particularly to devices, systems, and methods for treating obstetric and gynecological disorders other than urinary incontinence.

BACKGROUND

Although women are half of the U.S. population, women's health disorders have historically received far less attention than men's. The Agency for Health Care Policy and Research (AHCPR) cites studies indicating that one in four women ages 30-59 has experienced urinary incontinence alone. AHCPR estimates that the annual costs for caring for women with urinary incontinence are $11.2 billion. As many as 40% of women may experience mental health disturbances related to reproductive function, and nearly 40 million American women experience some form of sexual dysfunction.

SUMMARY

The present disclosure relates generally to neuromodulatory devices, systems and methods, and more particularly to devices, systems, and methods for treating obstetric and gynecological disorders other than urinary incontinence.

One aspect of the present disclosure relates to a therapy delivery device for treating an obstetric or gynecological disorder other than urinary incontinence in a subject. The therapy delivery device can comprise a housing, at least one electrode, and a power source. The housing can be configured for implantation in a reproductive system of the subject. The at least one electrode can be connected to the housing and be configured to deliver an electrical signal to an autonomic nervous system (ANS) nerve target. The power source can be in electrical communication with the at least one electrode.

Another aspect of the present disclosure relates to a therapy delivery device for treating an obstetric or gynecological disorder other than urinary incontinence in a subject. The therapy delivery can comprise a housing, at least one electrode, and a power source. The housing can be configured for implantation in a uterus, a vagina, an ovary, a fallopian tube, or a cervix of the subject. The at least one electrode can be connected to the housing and be configured to deliver an electrical signal to a sympathetic nerve target. The power source can be in electrical communication with the at least one electrode.

Another aspect of the present disclosure relates to a closed-loop therapy delivery system for treating an obstetric or gynecological disorder other than urinary incontinence in a subject. The therapy delivery system can comprise a housing, at least one electrode, a power source, a sensing component, and a controller. The housing can be configured for implantation in a reproductive system of the subject. The at least one electrode can be connected to the housing and be configured to deliver an electrical signal to an ANS nerve target. The power source can be in electrical communication with the at least one electrode. The sensing component can be configured to detect at least one physiological parameter associated with the obstetric or gynecological disorder. The controller can be configured to automatically coordinate operation of the power source and the sensing component. The controller can also be configured to direct delivery of the electrical signal to the at least one electrode to modulate activity of the ANS nerve target.

Another aspect of the present disclosure relates to a method for treating an obstetric or gynecological disorder other than urinary incontinence in a subject. One step of the method can include providing a therapy delivery device. The therapy delivery device can include a housing, at least one electrode connected to the housing, and a power source in electrical communication with the at least one electrode. Next, the therapy delivery device can be placed into a reproductive system of the subject so that the at least one electrode is in electrical communication with an ANS nerve target. The therapy delivery device can then be activated to deliver an electrical signal to the ANS nerve target to modulate activity at the ANS nerve target and thereby treat the obstetric or gynecological disorder.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIGS. 3A-D are a series of schematic illustrations showing alternative perspectives of the female reproductive system and its autonomic innervations;

DETAILED DESCRIPTION

Definitions

Figure 1:
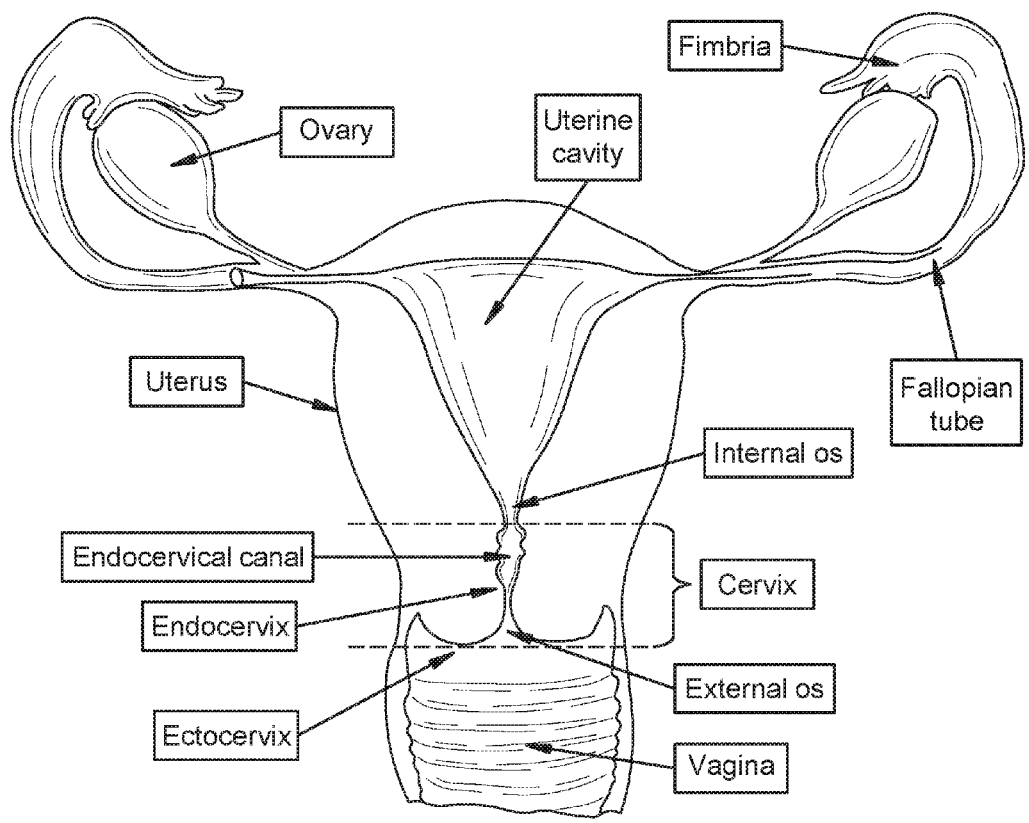
FIG. 1 is schematic illustration of the female reproductive system.
Figure 2:
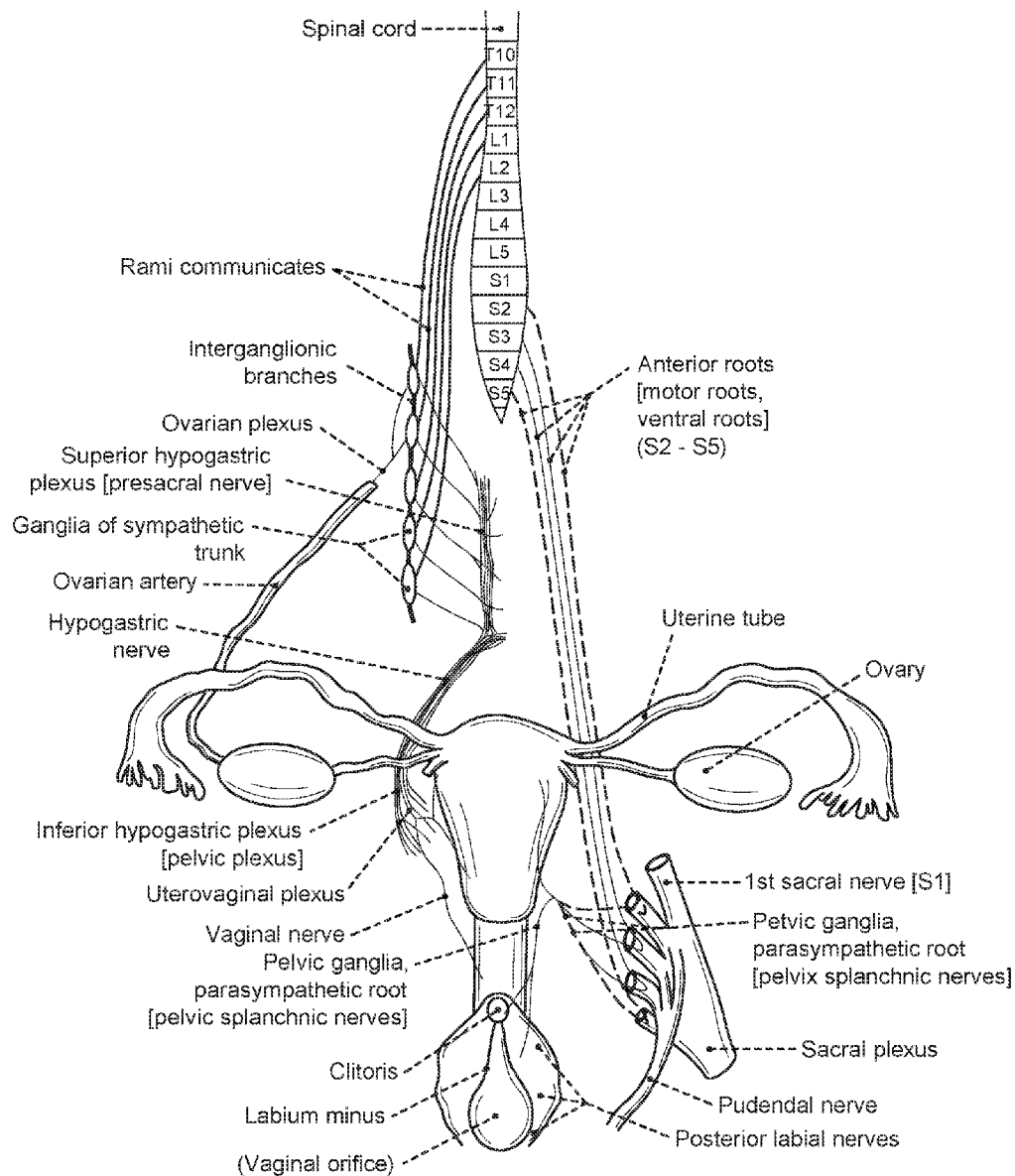
FIG. 2 is a schematic illustration showing the autonomic innervations of the female reproductive system.
Figure 3C:
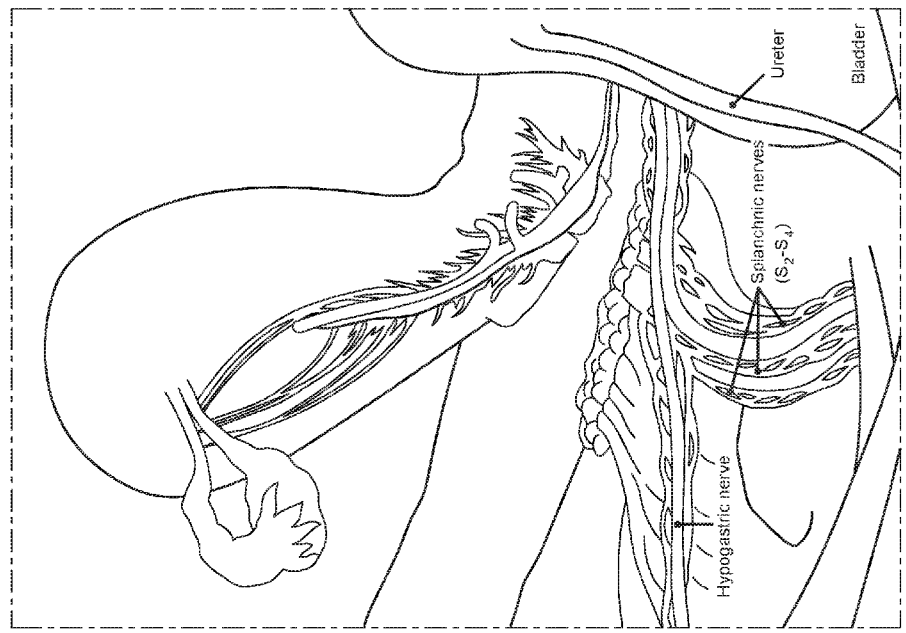
Figure 3D:
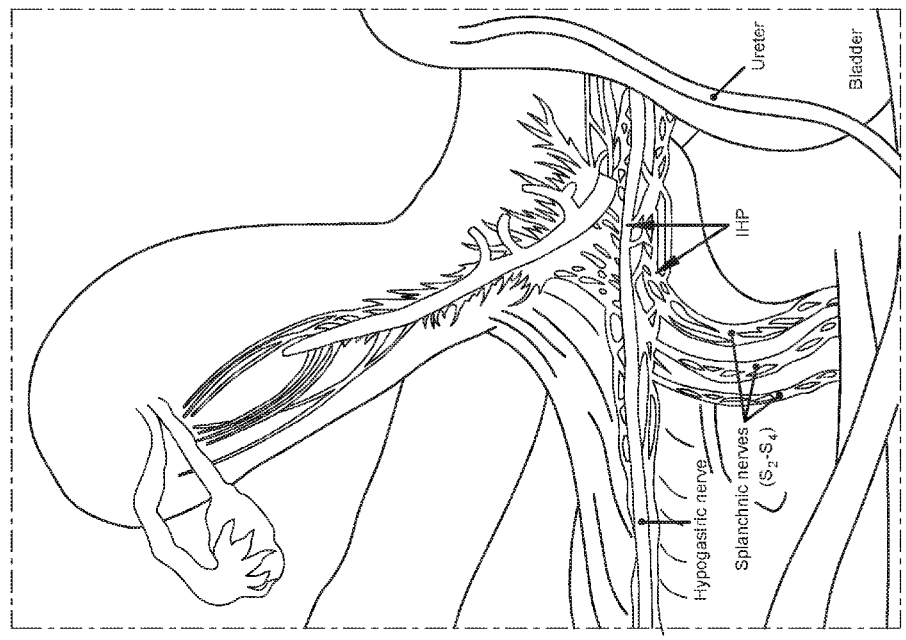
Figure 4:
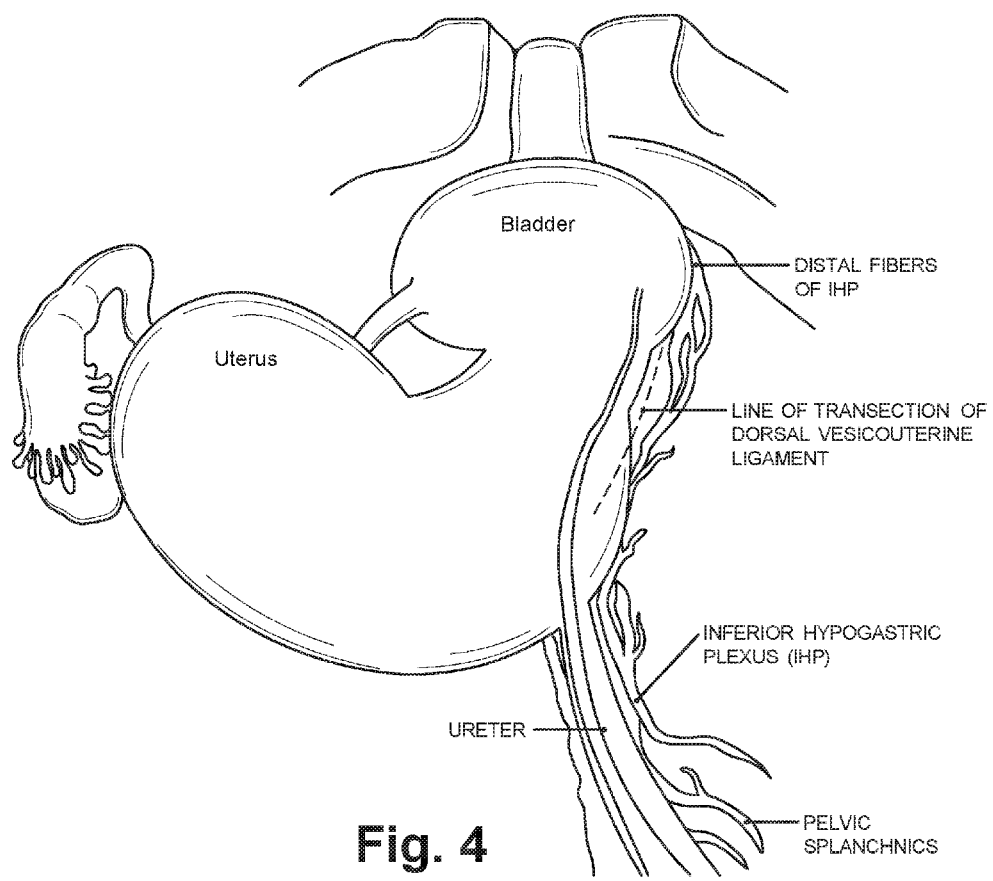
FIG. 4 is a schematic illustration showing another alternative perspective of the female reproductive system and its autonomic innervations.

Unless defined otherwise, all technical and scientific terms used herein have the same meaning as is commonly understood by one of skill in the art to which the present disclosure pertains.

In the context of the present disclosure, the terms "autonomic nervous system nerve target" or "ANS nerve target" can refer to any tissues of the sympathetic nervous system (SNS) or parasympathetic nervous system (PNS) including, but not limited to, neurons, axons, fibers, tracts, nerves, plexus, afferent plexus fibers, efferent plexus fibers, ganglia, chain, pre-ganglionic fibers, post-ganglionic fibers, afferents, efferents, and combinations thereof, whose activity can be modulated by the present disclosure. This also includes the spinal cord, DRG, and the plexus and nerve fibers associated with blood vessels.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, farm animals, livestock, etc.

As used herein, the terms "modulate" or "modulating" with reference to an ANS nerve target can refer to causing a change in neuronal activity, chemistry and/or metabolism. The change can refer to an increase, decrease, or even a change in a pattern of neuronal activity. The terms may refer to either excitatory or inhibitory stimulation, or a combination thereof, and may be at least electrical, magnetic, optical or chemical, ultrasound, infrared, or a combination of two or more of these. The terms "modulate" or "modulating" can also be used to refer to a masking, altering, overriding, regulating, synchronizing, controlling, changing, optimizing, or restoring of neuronal activity.

As used herein, the terms "substantially blocked" or "substantially block" when used with reference to activity at or associated with an ANS nerve target can refer to a complete (e.g., 100%) or partial inhibition (e.g., less than 100%, such as about 90%, about 80%, about 70%, about 60%, or less than about 50%) of nerve conduction through the ANS nerve target.

As used herein, the term "activity" when used with reference to an ANS nerve target can, in some instances, refer to the ability of a sympathetic or parasympathetic nerve, neuron, or fiber to conduct, propagate, and/or generate an action potential. In other instances, the term can refer to the frequency at which a nerve or neuron is conducting, propagating, and/or generating one or more action potentials at a given moment in time. In further instances, the term can refer to the frequency at which a nerve or neuron is conducting, propagating, and/or generating one or more action potentials over a given period of time (e.g., seconds, minutes, hours, days, etc.).

As used herein, the term "electrical communication" can refer to the ability of an electric field generated by an electrode or electrode array to be transferred, or to have a neuromodulatory effect, within and/or on an ANS nerve target.

As used herein, the term "obstetric disorder" can refer to any disease or condition caused by, related to, or associated with pregnancy. Non-limiting examples of obstetric disorders can include abortion, abruption, breech birth, cephalopelvic disproportion, dermatoses of pregnancy, diabetes, eclampsia, ectopic pregnancy, gestational diabetes, HELLP syndrome, hypertension, intrauterine growth restriction, macrosomia, obstetric fistula, obstetric hemorrhage, pelvic girdle pain, placenta praevia, pre-eclampsia, premature birth, prolonged gestation, labor disorders, ovulation, infertility, preterm labor or prematurity, uterine rupture, fecal incontinence, and uterine incarceration.

As used herein, the term "gynecological disorder" can refer to any disease or condition that affects the female genital tract and/or reproductive organs. Non-limiting examples of gynecological disorders can include abnormal menstrual periods, abnormal pap smears, endometriosis, fibroids, menopause, ovarian masses, pelvic inflammatory disease, pelvic pain (e.g., visceral and uterine pain syndromes), polycystic ovarian syndrome, sexually transmitted diseases, urinary tract infections, uterine bleeding, vaginitis, sexual dysfunction (e.g., anorgasmia, dyspareunia, hypoactive desire and arousal disorders), amenorrhea, dysmenorrhea, vulvodynia, vaginismus, pre-menstrual stress, abnormal vaginal discharge, vaginal itching, cervical polyps, cervicitis, and pre-menstrual dysphoric disorder.

As used herein, the terms "treat" or "treating" can refer to therapeutically regulating, preventing, improving, alleviating the symptoms of, and/or reducing the effects of an obstetric and/or gynecological disorder. As such, treatment also includes situations where an obstetric and/or gynecological disorder, or at least symptoms associated therewith, is completely inhibited, e.g., prevented from happening or stopped (e.g., terminated) such that the subject no longer suffers from the obstetric and/or gynecological disorder, or at least the symptoms that characterize the obstetric and/or gynecological disorder.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature may not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

Overview

A brief discussion of the pertinent neurophysiology is provided to assist the reader with understanding certain aspects of the present disclosure. The nervous system is divided into the somatic nervous system and the ANS. In general, the somatic nervous system controls organs under voluntary control (e.g., skeletal muscles) and the ANS controls individual organ function and homeostasis. For the most part, the ANS is not subject to voluntary control. The ANS is also commonly referred to as the visceral or automatic system.

The ANS can be viewed as a "real-time" regulator of physiological functions which extracts features from the environment and, based on that information, allocates an organism's internal resources to perform physiological functions for the benefit of the organism, e.g., responds to environment conditions in a manner that is advantageous to the organism. The ANS acts through a balance of its two components: the SNS and the PNS, which are two anatomically and functionally distinct systems. Both of these systems include myelinated preganglionic fibers which make synaptic connections with unmyelinated postganglionic fibers, and it is these fibers that then innervate the effector structure. These synapses usually occur in clusters called ganglia. Most organs are innervated by fibers from both divisions of the ANS, and the influence is usually opposing (e.g., the vagus nerve slows the heart, while the sympathetic nerves increase its rate and contractility), although it may be parallel (e.g., as in the case of the salivary glands). Each of these is briefly reviewed below.

The SNS is the part of the ANS comprising nerve fibers that leave the spinal cord in the thoracic and lumbar regions and supply viscera and blood vessels by way of a chain of sympathetic ganglia (also referred to as the sympathetic chain, sympathetic trunk or the gangliated cord) running on each side of the spinal column, which communicate with the central nervous system via a branch to a corresponding spinal nerve. The sympathetic trunks extend from the base of the skull to the coccyx. The cephalic end of each is continued upward through the carotid canal into the skull, and forms a plexus on the internal carotid artery; the caudal ends of the trunks converge and end in a single ganglion, the ganglion impar, placed in front of the coccyx.

The SNS controls a variety of autonomic functions including, but not limited to, control of movement and secretions from viscera and monitoring their physiological state, stimulation of the sympathetic system inducing, e.g., the contraction of gut sphincters, heart muscle and the muscle of artery walls, and the relaxation of gut smooth muscle and the circular muscles of the iris. The chief neurotransmitter in the SNS is adrenaline, which is liberated in the heart, visceral muscle, glands and internal vessels, with acetylcholine acting as a neurotransmitter at ganglionic synapses and at sympathetic terminals in skin and skeletal muscles. The actions of the SNS tend to be antagonistic to those of the PNS.

The neurotransmitter released by the post-ganglionic neurons is nonadrenaline (also called norepinephrine). The action of noradrenaline on a particular structure, such as a gland or muscle, is excitatory in some cases and inhibitory in others. At excitatory terminals, ATP may be released along with noradrenaline. Activation of the SNS may be characterized as general because a single pre-ganglionic neuron usually synapses with many post-ganglionic neurons, and the release of adrenaline from the adrenal medulla into the blood ensures that all the cells of the body will be exposed to sympathetic stimulation even if no post-ganglionic neurons reach them directly.

The PNS is the part of the ANS controlling a variety of autonomic functions including, but not limited to, involuntary muscular movement of blood vessels and gut and glandular secretions from eye, salivary glands, bladder, rectum and genital organs. The vagus nerve is part of the PNS. Parasympathetic nerve fibers are contained within the last five cranial nerves and the last three spinal nerves and terminate at parasympathetic ganglia near or in the organ they supply. The actions of the PNS are broadly antagonistic to those of the SNS—lowering blood pressure, slowing heartbeat, stimulating the process of digestion etc. The chief neurotransmitter in the PNS is acetylcholine. Neurons of the parasympathetic nervous system emerge from the brainstem as part of the Cranial nerves III, VII, IX and X (vagus nerve) and also from the sacral region of the spinal cord via Sacral nerves. Because of these origins, the PNS is often referred to as the "craniosacral outflow".

In the PNS, both pre- and post-ganglionic neurons are cholinergic (i.e., they utilize the neurotransmitter acetylcholine). Unlike adrenaline and noradrenaline, which the body takes around 90 minutes to metabolize, acetylcholine is rapidly broken down after release by the enzyme cholinesterase. As a result the effects are relatively brief in comparison to the SNS. Each pre-ganglionic parasympathetic neuron synapses with just a few post-ganglionic neurons, which are located near, or in, the effector organ, a muscle or gland. As noted above, the primary neurotransmitter in the PNS is acetylcholine such that acetylcholine is the neurotransmitter at all the pre- and many of the post-ganglionic neurons of the PNS. Some of the post-ganglionic neurons, however, release nitric oxide as their neurotransmitter.

As shown in FIGS. 1-4, the female reproductive system is innervated by the PNS and the SNS. The female reproductive organs can be subdivided into the internal and external genitalia. The internal genitalia are those organs that are within the true pelvis. These include the vagina, uterus, cervix, uterine tubes (oviducts or fallopian tubes), and ovaries. The external genitalia lie outside the true pelvis. These include the perineum, mons pubis, clitoris, urethral (urinary) meatus, labia majora and minora, vestibule, greater vestibular (Bartholin) glands, Skene glands, and periurethral area.

The vagina extends from the vulva externally to the uterine cervix internally. It is located within the pelvis, anterior to the rectum and posterior to the urinary bladder. The vagina lies at a 90° angle in relation to the uterus. The vagina is held in place by endopelvic fascia and ligaments. The vagina is lined by rugae, which are situated in folds throughout. These allow easy distention, especially during child bearing. The structure of the vagina is a network of connective, membranous, and erectile tissues. The pelvic diaphragm, the sphincter urethrae and transverse peroneus muscles, and the perineal membrane support the vagina. The sphincter urethrae and the transverse peroneus are innervated by perineal branches of the pudendal nerve. The pelvic diaphragm primarily refers to the levator ani and the coccygeus and is innervated by branches of sacral nerves S2-S4.

The nerve supply to the vagina is primarily from the ANS. Sensory fibers to the lower vagina arise from the pudendal nerve, and pain fibers are from sacral nerve roots.

The uterus is the inverted pear-shaped female reproductive organ that lies in the midline of the body, within the pelvis between the bladder and the rectum. It is thick-walled and muscular, with a lining that, during reproductive years, changes in response to hormone stimulation throughout a woman's monthly cycle. The uterus can be divided into 2 parts: the most inferior aspect is the cervix; and the bulk of the organ is called the body of the uterus (corpus uteri). Between these two is the isthmus, a short area of constriction. The body of the uterus is globe-shaped and is typically situated in an anteverted position, at a 90° angle to the vagina. The upper aspect of the body is dome-shaped and is called the fundus; it is typically the most muscular part of the uterus. The body of the uterus is responsible for holding a pregnancy, and strong uterine wall contractions help to expel the fetus during labor and delivery.

The vasculature of the uterus is derived from the uterine arteries and veins. The uterine vessels arise from the anterior division of the internal iliac, and branches of the uterine artery anastomose with the ovarian artery along the uterine tube. The nerve supply and lymphatic drainage of the uterus are complex. Lymphatic drainage is primarily to the lateral aortic, pelvic, and iliac nodes that surround the iliac vessels. The nerve supply is attained through the SNS (by way of the hypogastric and ovarian plexuses) and the PNS (by way of the pelvic splanchnic nerves from the second through fourth sacral nerves).

The cervix is the inferior portion of the uterus, separating the body of the uterus from the vagina. The cervix is cylindrical in shape, with an endocervical canal located in the midline, allowing passage of semen into the uterus. The external opening into the vagina is termed the external os, and the internal opening into the endometrial cavity is termed the internal os. The internal os is the portion of a female cervix that dilates to allow delivery of the fetus during labor. The vasculature is supplied by descending branches of the uterine artery, which run bilaterally at the 3 o'clock and 9 o'clock position of the cervix. The nerve supply to the cervix is via the PNS by way of the second through fourth sacral segments. Many pain nerve fibers run alongside these parasympathetics. Lymphatic drainage of the cervix is complex. The obturator, common iliac, internal iliac, external iliac, and visceral parametrial nodes are the main drainage points.

The present disclosure relates generally to neuromodulatory devices, systems and methods, and more particularly to devices, systems, and methods for treating obstetric and gynecological disorders other than urinary incontinence. The ANS regulates the intrinsic function and balance of each body organ, including the female reproductive system (e.g., the uterus, cervix, vagina, external genitalia and ovaries) and the components of the genitourinary (GU) system. As described in detail below, the present disclosure advantageously provides devices, systems, and methods for modulating the portion of the ANS that innervates the female reproductive and GU systems to effectively normalize, regulate, optimize, change, or modulate the ANS and thereby treat, prevent, retard, or reverse obstetric and/or gynecological disorders. By employing such devices, systems and methods, the present disclosure can treat obstetric and/or gynecological disorders by selectively modulating parasympathetic and/or sympathetic input and output of the female reproductive and GU systems.

Therapy Delivery Devices and Systems

In one aspect, the present disclosure includes various therapy delivery devices and related systems configured to treat an obstetric and/or gynecological disorder other than urinary incontinence in a subject. In some instances, therapy delivery devices that may be used to practice the present disclosure may be positioned directly on or in an ANS nerve target associated with an obstetric and/or gynecological disorder other than urinary incontinence. In other instances, therapy delivery devices that may be used to practice the present disclosure can be positioned below the skin of a subject but not directly on or in an ANS nerve target associated with an obstetric and/or gynecological disorder other than urinary incontinence. In further instances, therapy delivery devices that may be used to practice the present disclosure can comprise external devices, e.g., positioned in a lumen of the female reproductive tract (e.g., in the uterus, cervix or vagina) adjacent an ANS nerve target associated with an obstetric and/or gynecological disorder other than urinary incontinence. In still further instances, therapy delivery devices used to practice the present disclosure can comprise an external device, e.g., positioned on the skin of a subject adjacent an ANS nerve target associated with an obstetric and/or gynecological disorder other than urinary incontinence. Therapy delivery devices can be temporarily or permanently implanted within, on, or otherwise associated with a subject suffering from, afflicted by, or suspected of having an obstetric and/or gynecological disorder other than urinary incontinence.

Figure 5:
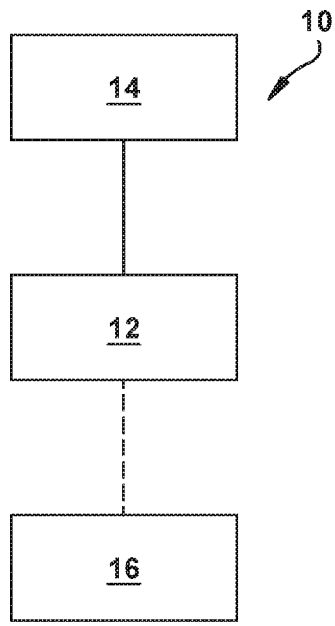
FIG. 5 is a block diagram illustrating a therapy delivery device according to one aspect of the present disclosure.

Therapy delivery devices of the present disclosure can be configured to deliver various types of therapy signals to target an ANS nerve target associated with an obstetric and/or gynecological disorder other than urinary incontinence. For example, therapy delivery devices of the present disclosure can be configured to deliver only electrical energy, only magnetic energy, only a pharmacological or biological agent, or a combination thereof. In one example, a therapy delivery device 10 (FIG. 5) of the present disclosure can comprise a housing 12 configured for implantation in a reproductive system of a subject, at least one electrode 14 that is connected to the housing and configured to deliver an electrical signal to an ANS nerve target, and an integral or remote power source 16, which is in electrical communication with the one or more electrodes and configured to produce one or more electrical signals (or pulses). In another example, therapy delivery devices can include a pharmacological or biological agent reservoir, a pump, and a fluid dispensing mechanism. Non-limiting examples of pharmacological and biological agents can include chemical compounds, drugs (e.g., prazosin, clonidine), nucleic acids, polypeptides, stem cells, toxins (e.g., botulinum), as well as various energy forms, such as ultrasound, radiofrequency (continuous or pulsed), magnetic waves, cryotherapy, and the like. In yet another example, therapy delivery devices can be configured to deliver magnetic nerve stimulation with desired field focality and depth of penetration. One skilled in the art will appreciate that combinations of the therapy delivery devices above configurations are also included within the scope of the present disclosure.

Figure 6:
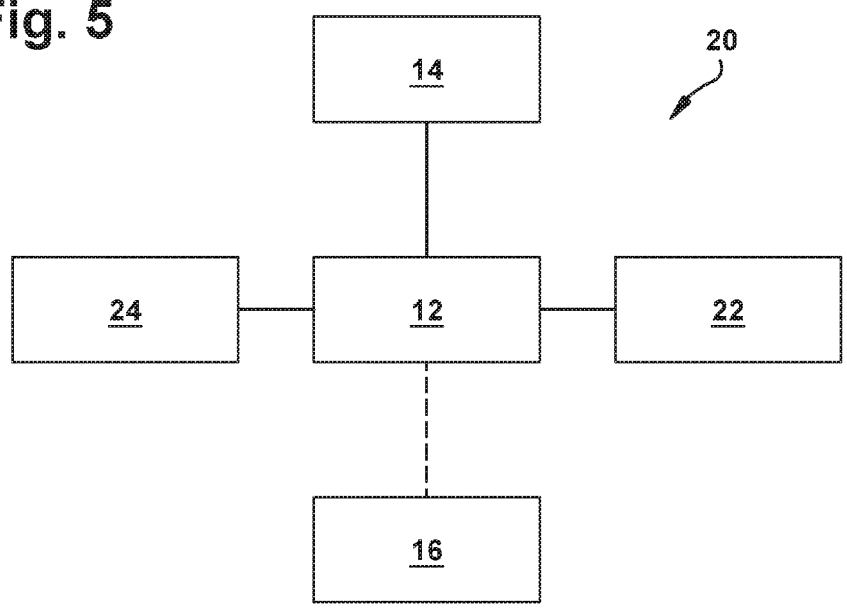
FIG. 6 is a block diagram illustrating a closed-loop therapy delivery system according to another aspect of the present disclosure.

In some instances, therapy delivery devices can comprise a stimulator (or inhibitor), such as an electrode, a controller or programmer, and one or more connectors (e.g., leads) for connecting the stimulating (or inhibiting) device to the controller. In one example, which is described in further detail below, the present disclosure can include a closed-loop therapy delivery system 20 (FIG. 6) for treating an obstetric and/or gynecological disorder other than urinary incontinence. As shown in FIG. 6, the therapy delivery system 20 can include a housing 12 configured for implantation in a reproductive system, at least one electrode 14 that is connected to the housing and configured to deliver an electrical signal to an ANS nerve target, a power source 16 in electrical communication with the at least one electrode, a sensing component 22 configured to detect at least one physiological parameter associated with the obstetric and/or gynecological disorder, and a controller 24 configured to automatically coordinate operation of the power source and the sensing component. Each of the sensing component 22, electrode 14, controller 24, and power source 16 can be in electrical communication with one another (e.g., via a physical connection, such as a lead, or a wireless link). In some instances, the sensing component 22 can comprise an electrode. In other instances, the electrode 14 can comprise a coil configured to deliver magnetic stimulation. In further describing representative electrodes, which are described in the singular, it will be apparent that more than one electrode may be used as part of a therapy delivery device. Accordingly, the description of a representative electrode suitable for use in the therapy delivery devices of the present disclosure is applicable to other electrodes that may be employed.

An electrode 14 can be controllable to provide output signals that may be varied in voltage, frequency, pulse-width, current and intensity. The electrode 14 can also provide both positive and negative current flow from the electrode and/or is capable of stopping current flow from the electrode and/or changing the direction of current flow from the electrode. In some instances, therapy delivery devices can include an electrode 14 that is controllable, i.e., in regards to producing positive and negative current flow from the electrode, stopping current flow from the electrode, changing direction of current flow from the electrode, and the like. In other instances, the electrode 14 has the capacity for variable output, linear output and short pulse-width, as well as paired pulses and various waveforms (e.g., sine wave, square wave, and the like).

The power source 16 can comprise a battery or generator, such as a pulse generator that is operatively connected to an electrode via the controller 24. The power source 16 can be configured to generate an electrical signal or signals. In one example, the power source 16 can include a battery that is rechargeable by inductive coupling. The power source 16 may be positioned in any suitable location, such as adjacent the electrode 14 (e.g., implanted adjacent the electrode), or a remote site in or on the subject's body or away from the subject's body in a remote location. An electrode 14 may be connected to the remotely positioned power source 16 using wires, e.g., which may be implanted at a site remote from the electrode(s) or positioned outside the subject's body. In one example, an implantable power source 16 analogous to a cardiac pacemaker may be used. In another example, the power source 16 can be located in a handheld device, such as a cell phone, or in an article of clothing, such as a belt or waistband.

The controller 24 can be configured to control the pulse waveform, the signal pulse width, the signal pulse frequency, the signal pulse phase, the signal pulse polarity, the signal pulse amplitude, the signal pulse intensity, the signal pulse duration, and combinations thereof of an electrical signal. The controller 24 may be used to convey a variety of currents and voltages to one or more electrodes 14 and thereby modulate the activity at an ANS nerve target. The controller 24 may be used to control numerous electrodes 14 independently or in various combinations as needed to provide stimulation or inhibition of nerve activity. In some instances, an electrode 14 may be employed that includes its own power source, e.g., which is capable of obtaining sufficient power for operation from surrounding tissues in the subject's body, or which may be powered by bringing a power source 16 external to the subject's body into contact with the subject's skin, or which may include an integral power source.

The electrical signal (or signals) delivered by the controller 24 to the electrode 14 may be constant, varying and/or modulated with respect to the current, voltage, pulse-width, cycle, frequency, amplitude, and so forth. For example, a current may range from about 0.001 to about 1000 microampere (mA) and, more specifically, from about 0.1 to about 100 mA. Similarly, the voltage may range from about 0.1 millivolt to about 25 volts, or about 0.5 to about 4000 Hz, with a pulse-width of about 10 to about 1000 microseconds. In one example, the electrical signal can be oscillatory. The type of stimulation may vary and involve different waveforms known to the skilled artisan. For example, the stimulation may be based on the H waveform found in nerve signals (i.e., Hoffman Reflex). In another example, different forms of interferential stimulation may be used.

To increase nerve activity in a portion of an ANS nerve target, for example, voltage or intensity may range from about 1 millivolt to about 1 volt or more, e.g., 0.1 to about 50 mA or volts (e.g., from about 0.2 volts to about 20 volts), and the frequency may range from about 1 Hz to about 10,000 Hz, e.g., about 1 Hz to about 1000 Hz (e.g., from about 2 Hz to about 100 Hz). In some instances, pure DC and/or AC voltages may be employed. The pulse-width may range from about 1 microsecond to about 10,000 microseconds or more, e.g., from about 10 microseconds to about 2000 microseconds (e.g., from about 15 microseconds to about 1000 microseconds). The electrical signal may be applied for at least about 1 millisecond or more, e.g., about 1 second (e.g., about several seconds). In some instances, stimulation may be applied for as long as about 1 minute or more, e.g., about several minutes or more (e.g., about 30 minutes or more).

To decrease activity in a portion of an ANS nerve target, for example, voltage or intensity may range from about 1 millivolt to about 1 volt or more, e.g., 0.1 to about 50 mA or volts (e.g., from about 0.2 volts to about 20 volts), and the frequency may range from about 1 Hz to about 10,000 Hz, e.g., about 50 Hz to about 2500 Hz. In one example, an electrical signal can have a frequency range of about 1000 Hz or greater (e.g., high frequency stimulation) to effectively block nerve conduction. In some instances, pure DC and/or AC voltages may be employed. The pulse-width may range from about 1 microseconds to about 10,000 microseconds or more, e.g., from about 10 microseconds to about 2000 microseconds (e.g., from about 15 microseconds to about 1000 microseconds). The electrical signal may be applied for at least about 1 millisecond or more, e.g., about 1 second (e.g., about several seconds). In some instances, the electrical energy may be applied for as long as about 1 minute or more, e.g., about several minutes or more (e.g., about 30 minutes or more may be used). In some instances, the controller 24 can be configured to deliver an electrical signal to the electrode 14 so that activity of an ANS nerve target is continuously and substantially blocked.

The electrode 14 may be mono-polar, bipolar or multi-polar. To minimize the risk of an immune response triggered by the subject against the therapy delivery device, and also to minimize damage thereto (e.g., corrosion from other biological fluids, etc.), the electrode 14 (and any wires and optional housing materials) can be made of inert materials, such as silicon, metal, plastic and the like. In one example, a therapy delivery device can include a multi-polar electrode 14 having about four exposed contacts (e.g., cylindrical contacts).

As discussed above, the controller 24 (or a programmer) may be associated with a therapy delivery device. The controller 24 can include, for example, one or more microprocessors under the control of a suitable software program. Other components of a controller 24, such as an analog-to-digital converter, etc., will be apparent to those of skill in the art. In some instances, the controller 24 can be configured to record and store data indicative of the intrinsic sympathetic or parasympathetic tone or activity in the subject. Therefore, the controller 24 can be configured to apply one or more electrical signals to the electrode 14 when the intrinsic sympathetic or parasympathetic tone or activity of a subject increases or decreases above a certain threshold value (or range of values). The controller 24 can be attached or connected to the housing 12 of a therapy delivery device 10 or, alternatively, the controller can be included as part of an external monitoring device (not shown), such as a handheld device (e.g., a cell phone). Such monitoring devices can be used by the subject and/or a medical practitioner to continuously monitor functioning of the therapy delivery device and/or signs and symptoms of the obstetric and/or gynecological disorder. In some instances, such monitoring devices can be programmed to adjust treatment parameters on demand or as part of a pre-programmed regimen.

Therapy delivery devices can be pre-programmed with desired stimulation parameters. Stimulation parameters can be controllable so that an electrical signal may be remotely modulated to desired settings without removal of the electrode 14 from its target position. Remote control may be performed, e.g., using conventional telemetry with an implanted power source 16, an implanted radiofrequency receiver coupled to an external transmitter, and the like. In some instances, some or all parameters of the electrode 14 may be controllable by the subject, e.g., without supervision by a physician. In other instances, some or all parameters of the electrode 14 may be automatically controllable by a controller 24.

In one example, a therapy delivery device can be configured for percutaneous placement or implantation. In this instance, the therapy delivery device can comprise one or more implantable electrodes shaped or configured, for example, as a wire, a rod, a filament, a ribbon, a cord, a tube, a formed wire, a flat strip, or a combination thereof. In one example, one or more of the electrodes can comprise a laminotomy electrode array. Laminotomy electrodes, for example, generally have a flat paddle configuration and typically possess a plurality of electrodes (e.g., 2, 3, 4 or more) arranged on the paddle. The arrangement of electrodes on the paddle may be in rows and columns, staggered, spaced, circular, or any other arrangement that will position the electrodes for optimal delivery of electrical energy. The one or more implantable electrodes may be controlled individually, in series, in parallel, or any other manner desired. Once implanted, the implantable electrode(s) may be held in position using any method known to the skilled artisan, such as stitches, epoxy, tape, glue, sutures, or a combination thereof.

In another example, a therapy delivery device can be configured for intravascular or intraluminal placement or implantation. In some instances, a therapy delivery device configured for intravascular or intraluminal placement or implantation can be configured in an identical or similar manner as the expandable electrode disclosed in U.S. patent application Ser. No. 11/641,331 to Greenberg et al. (hereinafter, "the '331 application"). In other instances, the therapy delivery device can be configured for intravascular or intraluminal placement or implantation at an implantation site that is adjacent, or directly adjacent, an ANS nerve target associated with an obstetric and/or gynecological disorder other than urinary incontinence. In one example, a therapy delivery device 10 can comprise a housing 12 configured for placement in a reproductive system (e.g., a uterus, a cervix, or a vagina of the subject) of a subject such that at least one electrode 14 of the therapy delivery device is in electrical communication with the ANS nerve target. In such instances, the therapy delivery device 10 can be configured similar or identical to a cervical cap, a cervical ring, a pessary, a tampon, a diaphragm, an intrauterine device, tocodynamometer, internal fetal scalp electrode, intrauterine pressure catheter, or any type of percutaneous electrode and/or transvaginal system.

In yet another example, a therapy delivery device can be configured for transcutaneous neuromodulation using magnetic stimulation. A magnetic stimulation device or system can generally include a pulse generator (e.g., a high current pulse generator) and a stimulating coil capable of producing magnetic pulses with desired field strengths. Other components of a magnetic stimulation device can include transformers, capacitors, microprocessors, safety interlocks, electronic switches, and the like. In operation, the discharge current flowing through the stimulating coil can generate the desired magnetic field or lines of force. As the lines of force cut through tissue (e.g., neural tissue), a current is generated in that tissue. If the induced current is of sufficient amplitude and duration such that the cell membrane is depolarized, nervous tissue will be stimulated in the same manner as conventional electrical stimulation. It is therefore worth noting that a magnetic field is simply the means by which an electrical current is generated within the nervous tissue, and that it is the electrical current, and not the magnetic field, which causes the depolarization of the cell membrane and thus stimulation of the target nervous tissue. Thus, in some instances, advantages of magnetic over electrical stimulation can include: reduced or sometimes no pain; access to nervous tissue covered by poorly conductive structures; and stimulation of nervous tissues lying deeper in the body without requiring invasive techniques or very high energy pulses.

In another example, transcutaneous neuromodulation can include positioning an electrode (or electrodes) on a skin surface so that an electrical signal (or magnetic field) can be delivered to an ANS nerve target associated with an obstetric and/or gynecological disorder other than urinary incontinence. Transcutaneous neuromodulation can additionally include partially transcutaneous methods (e.g., using a fine, needle-like electrode to pierce the epidermis). In other instances, a surface electrode (or electrodes) or magnetic coil can be placed into electrical communication with the ANS nerve target. In one example, a transcutaneous neuromodulation device can be configured to deliver an electrical signal to an ANS nerve target via transvaginal stimulation, transcervical stimulation, transabdominal stimulation, or transpelvic stimulation. Generally, an electrical signal used for transcutaneous neuromodulation may be constant, varying and/or modulated with respect to the current, voltage, pulse-width, cycle, frequency, amplitude, and so forth (e.g., the current may be between about 1 to 100 microampere), about 10 V (average), about 1 to about 1000 Hz or more, with a pulse-width of about 250 to about 500 microseconds.

Other examples of transcutaneous therapy delivery devices and systems that may be used as part of the present disclosure are described in U.S. Provisional Patent Application Ser. Nos. 61/693,946, filed Sep. 19, 2012, and 61/702,876, filed Aug. 28, 2012. It will be appreciated that transcutaneous therapy delivery devices and systems can additionally or optionally include any wearable item, accessory, article of clothing, or any object, device, or apparatus that a subject can use and, during use, comes into close or direct contact with a portion of the subject's body (e.g., the subject's neck). Examples of such transcutaneous neuromodulation devices can include vests, sleeves, shirts, socks, shoes, underwear, belts, scarves, wrist bands, gloves, ear pieces, band-aids, turtle neck, pendants, buttons, earrings, stickers, patches, bio-films, skin tattoos (e.g., using neuro-paint), chairs, computers, beds, head rests (e.g., of a chair or car seat), cell phones, and the like.

Therapy delivery devices can be part of an open- or closed-loop system. In an open-loop system, for example, a physician or subject may, at any time, manually or by the use of pumps, motorized elements, etc., adjust treatment parameters, such as pulse amplitude, pulse-width, pulse frequency, duty cycle, dosage amount, type of pharmacological or biological agent, etc. Alternatively, in a closed-loop system 20 (as discussed above), treatment parameters (e.g., electrical signals) may be automatically adjusted in response to a sensed physiological parameter or a related symptom or sign indicative of the extent and/or presence of an obstetric and/or gynecological disorder. In a closed-loop feedback system 20, a sensing component 22 can comprise a sensor (not shown in detail) that senses a physiological parameter associated with an obstetric and/or gynecological disorder can be utilized. More detailed descriptions of sensors that may be employed in closed-loop systems, as well as other examples of sensors and feedback control techniques that may be employed as part of the present disclosure are disclosed in U.S. Pat. No. 5,716,377. One or more sensing components 22 can be implanted on or in any tissue or organ of a subject. For example, a sensing component 22 can be implanted in or on a component of the ANS, such as nerves, ganglia, afferents or efferents, or the spinal cord. Alternatively or additionally, a sensing component 22 can be implanted on or in a structure or component of the female reproductive system or GU system.

It should be appreciated that implementing a therapy delivery device as part of a closed-loop system can include placing or implanting a therapy delivery device on or within a subject at an ANS nerve target associated with an obstetric and/or gynecological disorder other than urinary incontinence, sensing a physiological parameter associated with the obstetric and/or gynecological disorder, activating the therapy delivery device to apply an electrical signal to the ANS nerve target, and adjusting application of the electrical signal to the ANS nerve target in response to the sensor signal. In some instances, such physiological parameters can include any characteristic, sign, symptom, or function associated with an obstetric and/or gynecological disorder, such as a chemical moiety or nerve activity (e.g., electrical activity). Examples of such chemical moieties and nerve activities can include the activity of a sympathetic or parasympathetic nerve or nerve structure (e.g., ganglia or a ganglion), protein concentrations, electrochemical gradients, hormones (e.g., prostaglandin levels), neuroendocrine markers, inflammatory mediators, electrolytes, laboratory values, vital signs (e.g., blood pressure), skin temperature, core temperature, serum markers, blood vessel dilation, catecholamines, markers of locomotor activity, optical or infrared indicia of cervical tissue, uterine contractions, follicle size, or other signs and biomarkers associated with the obstetric and/or gynecological disorder.

Methods

Another aspect of the present disclosure includes methods for treating an obstetric and/or gynecological disorder other than urinary incontinence in a subject. In general, methods of the present disclosure can include the steps of: providing a therapy delivery device; placing the therapy delivery device into a reproductive system of the subject so that the at least one electrode is in electrical communication with an ANS nerve target associated with an obstetric and/or gynecological disorder other than urinary incontinence; and activating the therapy delivery device to deliver an electrical signal to the ANS nerve target to modulate activity at the ANS nerve target and thereby treat the obstetric and/or gynecological disorder. Subjects treatable by the present disclosure can, in some instances, be diagnosed with (or suspected of having) an obstetric and/or gynecological disorder as well as, or optionally, one or more related or unrelated medical conditions. For example, methods of the present disclosure can be employed to treat fecal incontinence, improve fertility, normalize ovulation, regulate the menstrual cycle (e.g., for birth control), treat pain syndromes (e.g., visceral or uterine), and/or treat sexual dysfunction (e.g., anorgasmia, dyspareunia, hypoactive desire, arousal disorders, etc.).

In some instances, the step of placing a therapy delivery device (e.g., at least one electrode thereof) into electrical communication with an ANS nerve target can entail different surgical and/or medical techniques, depending upon the target, for example. In some instances, a therapy delivery device can be surgically placed into electrical communication with an ANS nerve target via a percutaneous or endoscopic route. In other instances, a therapy delivery device can be placed into electrical communication with an ANS nerve target via an intravascular or intraluminal route. In further instances, a therapy delivery device can be placed into electrical communication with an ANS nerve target via a transcutaneous approach.

In some instances, a therapy delivery device can be placed into a reproductive or GU system of a subject so that at least one electrode thereof is in electrical communication with a parasympathetic nerve, such as a pelvic splanchnic nerve, an efferent parasympathetic fiber thereof, or an afferent parasympathetic fiber thereof. In other instances, a therapy delivery device can be placed into a reproductive or GU system of a subject so that at least one electrode thereof is in electrical communication with a sympathetic nerve, such as a hypogastric nerve, a hypogastric plexus (e.g., an inferior hypogastric plexus), a uterovaginal plexus, a T10-L1 sympathetic ganglion, a pelvic sympathetic ganglion, a pudendal nerve, an efferent sympathetic fiber thereof, or an afferent sympathetic fiber thereof.

After placing the therapy delivery device, the therapy delivery device can be activated to deliver an electrical signal to the ANS nerve target and thereby modulate the activity of the ANS nerve target. In some instances, delivery of an electrical signal to the ANS nerve target can completely or substantially block or modulate the activity at the ANS nerve target. Therefore, in such instances, delivery of an electrical signal to the ANS nerve target can prevent a sign and/or symptom associated with an obstetric and/or gynecological disorder from either increasing or decreasing (as compared to a control or baseline). In other instances, delivery of an electrical signal to the ANS nerve target can cause a sign and/or symptom associated with an obstetric and/or gynecological disorder to decrease (as compared to a control or baseline). The therapy delivery device can be activated at the onset of a sign and/or symptom associated with an obstetric and/or gynecological disorder or, alternatively, the therapy delivery device can be activated continuously or intermittently to reduce or eliminate the frequency of such sign(s) and/or symptom(s).

Delivery of the electrical signal to the ANS nerve target can affect central motor output, nerve conduction, neurotransmitter release, synaptic transmission, and/or receptor activation. For example, a sympathetic nerve may be electrically modulated to alter, shift, or change sympathetic activity from a first state to a second state, where the second state is characterized by a decrease in sympathetic activity relative to the first state. As discussed above, delivery of an electrical signal to the ANS nerve target can substantially block activity of the ANS nerve target. In some instances, delivery of the electrical signal to the ANS nerve target can achieve a complete nerve conduction block of the ANS nerve target for a desired period of time. In other instances, delivery of the electrical signal to the ANS nerve target can achieve a partial block of the ANS nerve target for a period of time that is long enough to decrease activity therein. The degree to which activity of the ANS nerve target is modulated can be titrated by one skilled in the art depending, for example, upon the nature and severity of the obstetric and/or gynecological disorder in the subject.

Figure 7:
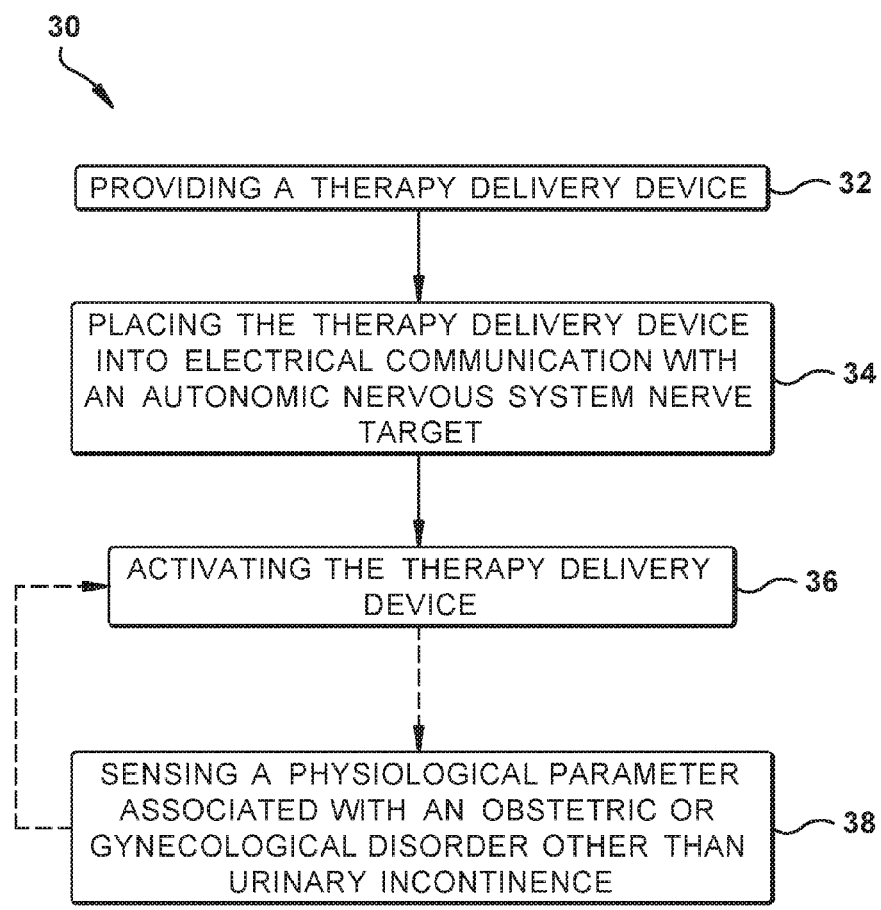
FIG. 7 is a process flow diagram illustrating a method for treating an obstetric or gynecological condition other than urinary incontinence according to another aspect of the present disclosure.

In another aspect, the present disclosure can include a method 30 (FIG. 7) for treating an obstetric and/or gynecological disorder other than urinary incontinence in a subject. One step of the method 30 can include providing a therapy delivery device 10 (Step 32). In one example, the therapy delivery device 10 can comprise an electrode array configured for percutaneous implantation in the subject. At Step 34, the therapy delivery device 10 can be placed into direct electrical contact with an ANS nerve target. In some instances, "direct electrical contact" can mean that the therapy delivery device 10 is placed on or in the ANS nerve target. In other instances, "direct electrical contact" can mean that the therapy delivery device 10 is located adjacent or directly adjacent (but not in physical contact with) the ANS nerve target such that delivery of an electrical signal can modulate a function, activity, and/or characteristic of the ANS nerve target.

After placing the therapy delivery device 10 into direct electrical contact with the ANS nerve target, an electrical signal is delivered to the ANS nerve target (Step 36). The therapy signal can be delivered in an amount and for a time sufficient to modulate activity at the ANS nerve target and thereby treat the obstetric and/or gynecological disorder. In one example, an electrical signal can be delivered to a pelvic splanchnic nerve by an electrode or electrode array that is placed directly on or in the nerve. In such instances, an electrical signal can be delivered to the pelvic splanchnic nerve continuously, periodically, or on an as needed basis to increase parasympathetic activity and thereby increase vaginal secretion production, improve orgasmic contraction of the uterus and vagina, and/or improve sexual sensation in the subject.

Another aspect of the method 30 includes sensing a physiological parameter associated with the obstetric and/or gynecological disorder (Step 38). To this end, the method 30 can further include providing (and placing) a closed-loop therapy delivery system 20 (as described above). In one example, the closed-loop therapy system 20 can be configured for percutaneous implantation in the subject. Once the system 20 is implanted, the sensing component 22 can detect a physiological parameter of interest, such as electrical activity of the ANS nerve target (or a different nerve target), which may be indicative of intrinsic sympathetic or parasympathetic tone in the subject. The detected level(s) of electrical activity can then be relayed to the controller 24, which determines if the detected level(s) is/are within a normal or abnormal range or level. Where the detected level(s) is/are within an abnormal range (e.g., at an elevated or decreased level as compared to a control or baseline), the controller 24 can cause the power source 16 to deliver an electrical signal to the at least one electrode 14. The electrical signal is then delivered to the ANS nerve target to modulate activity thereof. While the electrical signal(s) is/are being delivered to the ANS nerve target, the sensing component 22 can continue to detect the level of electrical activity within the ANS nerve target (or other nerve target). When the level of electrical activity in the ANS nerve target is equal, or about equal to, a normal or baseline level, the controller 24 can cease delivery of the electrical signal(s) to the electrode 14. By continuously or intermittently monitoring the intrinsic sympathetic or parasympathetic tone or activity of the subject, the closed-loop therapy delivery system 20 can automatically normalize autonomic activity and thus effectively treat the obstetric and/or gynecological disorder.

Another aspect of the present disclosure can include transvascular or transluminal delivery of an electrical energy to an ANS nerve target associated with an obstetric and/or gynecological disorder other than urinary incontinence. Thus, in some instances, the method 30 can include providing a therapy delivery device configured for transvascular or transluminal insertion and placement within the subject. For instance, a therapy delivery device configured for intravascular placement in a subject can include an expandable electrode as disclosed in the '331 application. In another example, a therapy delivery device can be configured for placement in a reproductive or GU system of a subject. In such instances, the therapy delivery device can be configured similar or identical to a cervical cap, a cervical ring, a pessary, a diaphragm, an intrauterine device, or any type of percutaneous electrode and/or transvaginal system. Non-limiting examples of vessel and lumens into which the therapy delivery device can be inserted include vasculature supplying the female reproductive and GU systems, such as arteries (e.g., an internal iliac artery), veins, a vagina, a cervix, a uterus, a rectum, or any other bodily orifice. The therapy delivery device can be surgically inserted into the vessel or lumen via a percutaneous, transvascular, laparoscopic, or open surgical procedure.

Figure 8:
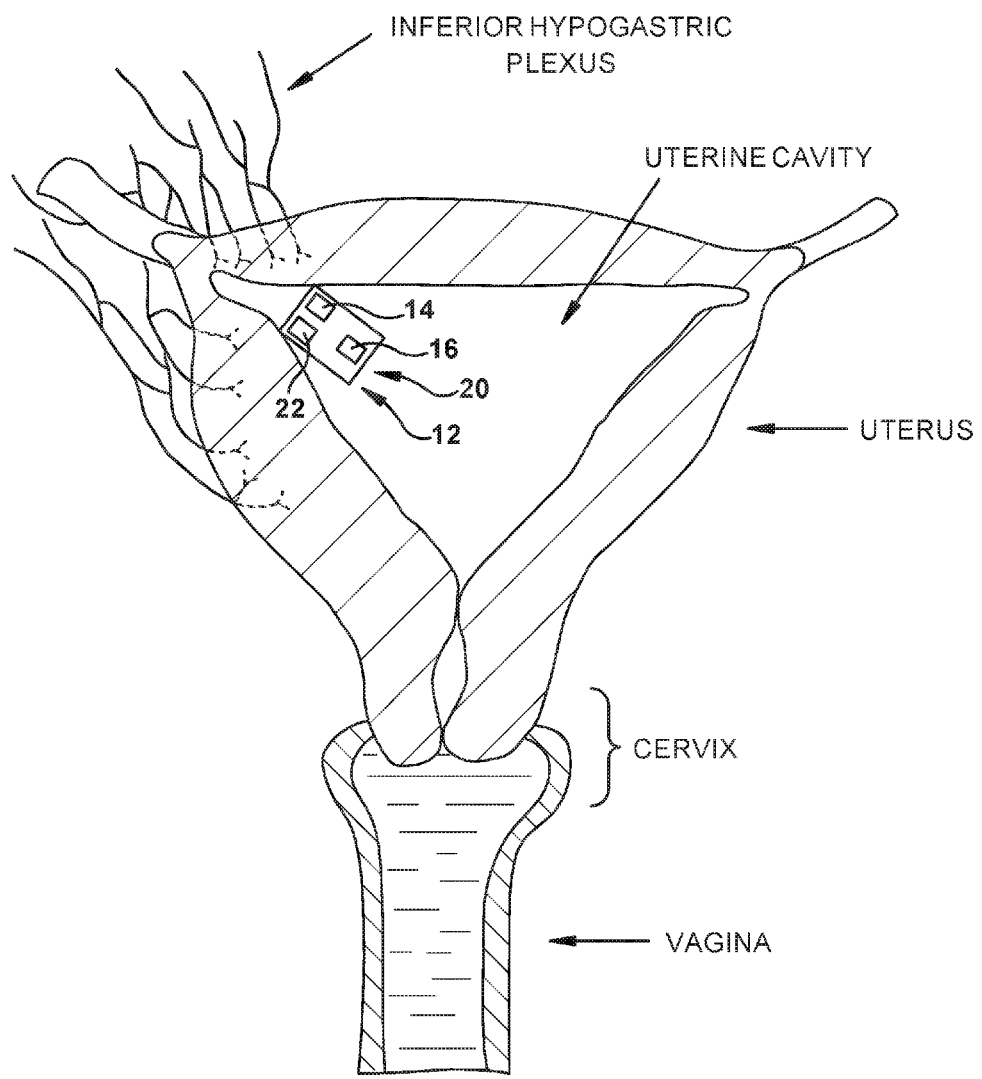
FIG. 8 is a schematic illustration showing a therapy delivery device implanted in a uterus of a subject suffering from an obstetric or gynecological disorder other than urinary incontinence.

In one example of the present disclosure, a therapy delivery system 20 can be inserted into the uterus of a subject (FIG. 8).

After inserting the therapy delivery device into the vessel or lumen, the therapy delivery device can be advanced (if needed) to an intraluminal target site so that the therapy delivery device is in electrical communication with the ANS nerve target. In some instances, advancement of the therapy delivery device can be done under image guidance (e.g., fluoroscopy, CT, MRI, etc.). Intraluminal target sites can include intravascular or intraluminal locations at which the therapy delivery device is capable of being positioned or implanted without damage or functional impairment to the subject. For example, an intraluminal target site can include a portion of a vessel or luminal wall that is innervated by (or in electrical communication with) an ANS nerve target, such as neurons, axons, fibers, tracts, nerves, plexus, afferent plexus fibers, efferent plexus fibers, ganglion, pre-ganglionic fibers, and post-ganglionic fibers of the ANS associated with an obstetric and/or gynecological disorder.

In one example, the therapy delivery system 20 can be positioned in a uterus of a subject (as shown in FIG. 8) so that at least one electrode 14 of the system is in electrical communication with an ANS nerve target, such as one or more fibers of the inferior hypogastric plexus.

After placing the therapy delivery device, an electrical signal can be delivered to the ANS nerve target. The therapy signal can be delivered in an amount and for a time sufficient to modulate activity in or at the ANS nerve target and thereby treat the obstetric and/or gynecological disorder.

In another aspect, the method 30 can include providing a therapy delivery device configured for placement on the skin of the mammal. For example, a therapy delivery device can be configured for transabdominal or transpelvic delivery of an electrical signal to an ANS nerve target associated with an obstetric and/or gynecological disorder. In some instances, the therapy delivery device can be positioned about the subject, without penetrating the skin of the subject, so that the therapy delivery device is in electrical communication with the ANS nerve target. Non-limiting examples of ANS nerve targets into which the therapy delivery device can be placed into electrical communication with can include a parasympathetic nerve, such as a pelvic splanchnic nerve, an efferent parasympathetic fiber thereof, or an afferent parasympathetic fiber thereof, a sympathetic nerve, such as a hypogastric nerve, a hypogastric plexus (e.g., an inferior hypogastric plexus), a uterovaginal plexus, a T10-L1 sympathetic ganglion, a pelvic sympathetic ganglion, a pudendal nerve, an efferent sympathetic fiber thereof, or an afferent sympathetic fiber thereof.

After placing the therapy delivery device, an electrical signal is delivered to the ANS nerve target. The therapy signal can be delivered in an amount and for a time sufficient to modulate activity in or at the ANS nerve target and thereby treat the obstetric and/or gynecological disorder. It will be appreciated that a system 20 (as described above) can be implanted via an intravascular or intraluminal approach to enable closed-loop treatment of an obstetric and/or gynecological disorder.

From the above description of the present disclosure, those skilled in the art will perceive improvements, changes and modifications. For example, nerve targets other than, or in addition to, ANS nerve targets can include spinal tissue, such as the spinal cord, spinal dorsal columns, ventral and dorsal spinal cord nerves, and dorsal root ganglia. Such improvements, changes, and modifications are within the skill of those in the art and are intended to be covered by the appended claims. All patents, patent applications, and publication cited herein are incorporated by reference in their entirety.

The following is claimed:

1. A therapy delivery system for treating an obstetric or gynecological disorder other than urinary incontinence in a subject, the therapy delivery system comprising:
    a housing configured for transvaginal, transcervical, or transabdominal stimulation, or transpelvic placement on a subject's skin;
    at least one electrode connected to the housing and configured to deliver an electrical signal to an autonomic nervous system (ANS) nerve target; and
    a controller programmed to direct delivery of the electrical signal to the at least one electrode to modulate activity at the ANS nerve target site to treat the obstetric or gynecological disorder.

2. The therapy delivery system of claim 1, wherein the housing is configured for transcutaneous placement on a uterus, a vagina, an ovary, a fallopian tube, or a cervix of the subject.

3. The therapy delivery system of claim 1, wherein the controller is programmed to delivery an electrical signal having a frequency of about 1000 Hz or greater.

4. The therapy delivery system of claim 1, wherein the ANS nerve target is a parasympathetic nerve.

5. The therapy delivery system of claim 4, wherein the parasympathetic nerve is a pelvic splanchnic nerve.

6. The therapy delivery system of claim 1, wherein the ANS nerve target is sympathetic nerve.

7. The therapy delivery system of claim 6, wherein the sympathetic nerve is a hypogastric nerve, a hypogastric plexus, an inferior hypogastric plexus, a uterovaginal plexus, a T10-L 1 sympathetic ganglion, a pudendal nerve, an efferent sympathetic fiber thereof, or an afferent sympathetic fiber thereof.

8. The therapy delivery system of claim 1, wherein the obstetric or gynecological disorder is pre-term labor.

9. A therapy delivery system for treating an obstetric or gynecological disorder other than urinary incontinence in a subject, the therapy delivery system comprising:
    a housing configured for transcutaneous placement on a uterus, a vagina, an ovary, a fallopian tube, or a cervix of the subject;
    at least one electrode connected to the housing and configured to deliver an electrical signal to a sympathetic nerve target; and
    a controller programmed to direct delivery of the electrical signal to the at least one electrode to modulate activity at the sympathetic nerve target to treat the obstetric or gynecological disorder.

10. A method for treating an obstetric or gynecological disorder other than urinary incontinence in a subject, the method comprising:
    providing a therapy delivery device, the therapy delivery device including a housing, at least one electrode connected to the housing, and a power source in electrical communication with the at least one electrode;
    transcutaneously placing the therapy delivery device on a reproductive organ or tissue of the subject so that the at least one electrode is in electrical communication with an ANS nerve target; and
    activating the therapy delivery device to deliver an electrical signal to the ANS nerve target to modulate activity at the ANS nerve target to treat the obstetric or gynecological disorder.

11. The method of claim 10, wherein said providing further includes providing a closed-loop therapy delivery system, the system including a sensing component and a controller that are in communication with the housing, the sensing component being configured to detect at least one physiological parameter associated with the obstetric or gynecological disorder, the controller being configured to automatically coordinate operation of the power source and the sensing component.

12. The method of claim 11, further comprising:
    sensing at least one physiological parameter associated with the obstetric or gynecological disorder;
    generating a sensor signal based on the at least one physiological parameter; and activating the therapy delivery device to adjust application of the electrical signal to the ANS nerve target in response to the sensor signal to treat the obstetric or gynecological disorder.

13. The method of claim 10, wherein the obstetric or gynecological disorder is selected from the group consisting of pre-term labor, fecal incontinence, infertility, irregular menstrual cycle, polycystic ovary syndrome, dysmenorrhea, amenorrhea, sexual dysfunction, visceral pain syndromes, uterine pain syndromes, vulvodynia, vaginismus, pre-menstrual stress, and pre-menstrual dysphoric disorder.

14. The method of claim 10, wherein said placing further includes transcutaneously placing the housing on a uterus, a vagina, an ovary, a fallopian tube, or a cervix of the subject.

15. The method of claim 10, wherein the ANS nerve target is a parasympathetic nerve.

16. The method of claim 15, wherein the parasympathetic nerve is a pelvic splanchnic nerve.

17. The method of claim 10, wherein the ANS nerve target is a sympathetic nerve.

18. The method of claim 17, wherein the sympathetic nerve is a hypogastric nerve, a hypogastric plexus, an inferior hypogastric plexus, a uterovaginal plexus, a T10-L1 sympathetic ganglion, a pudenda! nerve, an efferent sympathetic fiber thereof, or an afferent sympathetic fiber thereof.

19. The method of claim 10, wherein the electrical signal has a frequency of about 10,000 Hz to about 25,000 Hz.

* * * * *